(12) United States Patent
Gilmore et al.

(10) Patent No.: US 9,192,728 B2
(45) Date of Patent: Nov. 24, 2015

(54) DRUG DELIVERY DEVICE

(75) Inventors: Stephen Francis Gilmore, Bristol (GB); Paul Richard Draper, Worcestershire (GB); Joseph Butler, Warwickshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/130,031

(22) PCT Filed: Jul. 12, 2012

(86) PCT No.: PCT/EP2012/063619
§ 371 (c)(1),
(2), (4) Date: Dec. 30, 2013

(87) PCT Pub. No.: WO2013/010884
PCT Pub. Date: Jan. 24, 2013

(65) Prior Publication Data
US 2014/0142511 A1 May 22, 2014

Related U.S. Application Data

(60) Provisional application No. 61/570,307, filed on Dec. 14, 2011.

(30) Foreign Application Priority Data

Jul. 15, 2011 (EP) .................................. 11174119

(51) Int. Cl.
*A61M 5/00* (2006.01)
*A61M 5/315* (2006.01)
(Continued)

(52) U.S. Cl.
CPC ....... *A61M 5/31568* (2013.01); *A61M 5/31551* (2013.01); *A61M 5/31585* (2013.01);
(Continued)

(58) Field of Classification Search
CPC ............. A61M 2005/2488; A61M 2005/3126; A61M 2205/52; A61M 5/31541; A61M 5/31551; A61M 5/31568; A61M 5/31585; A61M 5/31593; G01D 5/2497; G01D 5/25
USPC ........................................................ 604/189
See application file for complete search history.

(56) References Cited

U.S. PATENT DOCUMENTS

2007/0123829 A1  5/2007  Atterbury et al.
2010/0069748 A1  3/2010  Yamamoto
2011/0270214 A1*  11/2011  Jorgensen et al. ............ 604/500

FOREIGN PATENT DOCUMENTS

WO  2006/045523  5/2006
WO  2010/052275  5/2010
(Continued)

OTHER PUBLICATIONS

International Search Report for Int. App. No. PCT/EP2012/063619, completed Oct. 29, 2012.
(Continued)

*Primary Examiner* — Kevin C Sirmons
*Assistant Examiner* — Deanna K Hall
(74) *Attorney, Agent, or Firm* — McDonnell Boehnen Hulbert & Berghoff LLP (57) ABSTRACT

A drug delivery device is presented comprising of a housing, a plurality of contacts, a rod disposed within the housing, and an encoded member configured to be rotatably supported inside the housing, to engage with the rod and to be rotatable with respect to the rod, and to be axially constrained with respect to the housing such that axial advancement of the rod in a first direction relative to the housing causes rotation of the encoded member, wherein the outer surface of the encoded member is provided with a plurality of tracks together forming an encoder, each track comprising conductive segments and non-conductive segments and wherein the encoded member is supported in the housing such that each track is engaged by a respective one of the plurality of contacts.

15 Claims, 7 Drawing Sheets

(51) Int. Cl.
 *G01D 5/249* (2006.01)
 *G01D 5/25* (2006.01)
 *A61M 5/24* (2006.01)
 *A61M 5/31* (2006.01)

(52) U.S. Cl.
 CPC ......... *A61M5/31593* (2013.01); *G01D 5/2497* (2013.01); *G01D 5/25* (2013.01); *A61M 5/31541* (2013.01); *A61M 2005/2488* (2013.01); *A61M 2005/3126* (2013.01); *A61M 2205/52* (2013.01)

(56) References Cited

FOREIGN PATENT DOCUMENTS

WO 2010/098927 9/2010
WO 2010/139640 12/2010

OTHER PUBLICATIONS

European Search Report for EP App. No. 11174119.5, completed Mar. 21, 2012.

* cited by examiner

| Code No: | 1 | 2 | 3 | 4 | 5 | Results |
|---|---|---|---|---|---|---|
| 0 | ■ | ■ | ■ | ■ | ■ | 00000 |
| 1 | ■ | ■ | ■ | ■ | □ | 00001 |
| 2 | ■ | ■ | ■ | □ | □ | 00011 |
| 3 | ■ | ■ | ■ | □ | ■ | 00010 |
| 4 | ■ | ■ | □ | □ | ■ | 00110 |
| 5 | ■ | ■ | □ | □ | □ | 00111 |
| 6 | ■ | ■ | □ | ■ | □ | 00101 |
| 7 | ■ | ■ | □ | ■ | ■ | 00100 |
| 8 | ■ | □ | □ | ■ | ■ | 01100 |
| 9 | ■ | □ | □ | ■ | □ | 01101 |
| 10 | ■ | □ | □ | □ | □ | 01111 |
| 11 | ■ | □ | □ | □ | ■ | 01110 |
| 12 | ■ | □ | ■ | □ | ■ | 01010 |
| 13 | ■ | □ | ■ | □ | □ | 01011 |
| 14 | ■ | □ | ■ | ■ | □ | 01001 |
| 15 | ■ | □ | ■ | ■ | ■ | 01000 |
| 16 | □ | □ | ■ | ■ | ■ | 11000 |
| 17 | □ | □ | ■ | ■ | □ | 11001 |
| 18 | □ | □ | ■ | □ | □ | 11011 |
| 19 | □ | □ | ■ | □ | ■ | 11010 |
| 20 | □ | □ | □ | □ | ■ | 11110 |
| 21 | □ | ■ | □ | □ | ■ | 10110 |
| 22 | □ | ■ | □ | □ | □ | 10111 |
| 23 | □ | ■ | □ | ■ | □ | 10101 |
| 24 | ■ | ■ | ■ | ■ | ■ | 00000 |

DRUG DELIVERY DEVICE

CROSS REFERENCE TO RELATED APPLICATIONS

The present application is a U.S. National Phase Application pursuant to 35 U.S.C. §371 of International Application No. PCT/EP2012/063619 filed Jul. 12, 2012, which claims priority to European Patent Application No. 11174119.5 filed on Jul. 15, 2011, and U.S. Provisional Patent Application No. 61/570,307, filed Dec. 14, 2011. The entire disclosure contents of these applications are herewith incorporated by reference into the present application.

TECHNICAL FIELD

The present invention relates to a drug delivery device.

BACKGROUND

Pen type drug delivery devices have application where regular injection by persons without formal medical training occurs. This is increasingly common among patients having diabetes where self-treatment enables such patients to conduct effective management of their diabetes.

For good or perfect glycemic control, the dose of insulin or insulin glargine has to be adjusted for each individual in accordance with a blood glucose level to be achieved. The present invention relates to injectors, for example hand-held injectors, especially pen-type injectors, that is to injectors of the kind that provide for administration by injection of medicinal products from a multidose cartridge. In particular, the present invention relates to such injectors where a user may set the dose.

A user undertaking self-administration of insulin will commonly need to administer between 1 and 80 International Units.

SUMMARY

Drug delivery devices, e.g. pen-shaped syringes usually have a container of medicament with a piston at its one end and an opening at the other end, e.g. fluidly connected to an injection needle. Medicament is dispensed by a rod, spindle, or lead screw, or any other term used for describing the element pushing the piston. Hence determining the axial displacement of the rod that drives the piston enables measuring the volume of medicament dispensed from the container.

Sensing the movement of the rod provides a direct measure of the amount of medicament that is actually dispensed. In particular, dose setting or dose correction would not impact the measuring process.

According to the present invention, an encoded member comprises a coded array that provides for determining the relative rotational position of the member carrying the code. The coded array may comprise a binary code, e.g. comprising conductive and non-conductive segments. A corresponding plurality of contacts may be required to transmit signals to a processor. Further, a coded array may comprise black and white segments providing an optical encoding. Accordingly, a corresponding plurality of light sensors is required to transmit signals to a processor.

Having the encoded member threadedly engaged with a rod, the angle of rotation of the encoded member is a function of the axial displacement of the rod and may be determined by the pitch of the thread. Hence, the rotational position of the encoded member may provide a measure for the axial displacement of the rod. For example, for a constant pitch, the angle of rotation of the encoded member is proportional to the axial displacement of the rod.

The amount of rotation of the encoded member of the present invention provides a measure for the axial displacement of a piston rod and therefore for the amount of medicament dispensed in response to the axial displacement of the rod.

In one embodiment, having a code comprising five tracks of conductive and non-conductive segments allows to resolve $2^5=32$ unique values that relate to rotational positions.

The axial displacement of the rod may be measured for rotating rods (e.g. spindles) having a combined movement of axial shift and rotation as well as for rods that do not rotate and only have an axial shift, e.g. similar to a plunger of a syringe.

In many drive mechanisms known in the art, the angular rotation of a rotating rod, e.g. a spindle, per dose unit may be determined by the pitch of the thread. It is common that the angular rotation of a rotating rod per dose unit is small. This gives the problem of creating a high accuracy demand for an encoder unit. The threaded engagement allows control of the relative rotational speed of the encoded member, e.g. a nut, relative to the spindle.

According to the invention, the pitch could be adapted to have the encoded member, e.g. a nut, rotate at a higher angular velocity as the spindle during drug dispense.

In one embodiment, an encoded member, e.g. a nut, rotates at an angular velocity that is twice the angular velocity of the spindle during drug dispense. Each of the segments of the coded array can be twice as large compared to an equivalent encoded nut, which rotates at the same speed as the spindle. An advantage of this feature is that the reliability of the angular position determination is increased.

For an insulin pen, where the user may select a dose between 1 and 80 international units (IUs), a seven bit code or encoding system would be sufficient ($2^8=128$) to represent the doses within one full rotation of the encoded member. Alternatively, a processor could be configured to allow determining multiple full rotations of the encoded member. This allows for a lower bit code, e.g. 5 bit code.

Engaging an encoded member rotatably with a piston rod and to be rotatable with respect to the rod provides a solution to encode the linear travel of a piston rod. The direct engagement between the encoded member and the piston rod may provide for improved accuracy and/or reliability. Another benefit is the reduced susceptibility to manufacturing tolerances.

Injection devices are known in the art that include a doseable quantity identifier that uses a rotational matrix and a sensor for electrically sensing the arrangement of the dose setting mechanism of the device. The devices, e.g. a pen, further comprise a switch provided in the injector, serving to distinguish between dosing and injecting operations. The switch is operably coupled to a dispense button.

However, there is the risk that the device may erroneously indicate either device mode, e.g. either dosing when an injection is performed, or injection when actually a dose is set. For example manufacturing tolerances may lead to the switch being electrically triggered into dose mode before a button has been pressed sufficiently far to mechanically change the clutching system. In this case a dose dispensed may be logged falsely, however the device only dials back to zero. This event of false logging could lead to medically serious situations for a user, because they may think having received a dose when actually they have not.

Some embodiments according to the present invention improve reliability of determining dispense and thus credibility of the medication logging or dose history. As the encoded member is coupled directly to the piston rod, the piston rod cannot move without the encoded member moving. Therefore, if the processor receives signals indicating rotation of the encoded member, the piston must be moving and a dose must be being dispensed.

Determining the dispensed dose in sensing the movement of the piston rod does not require a distinguishing mechanism, e.g. a switch, because the piston rod is only moved during dose dispense. The proposed solution according to the invention therefore also reduces complexity and cost of implementation.

A first aspect of the invention provides a drug delivery device comprising:
 a housing;
 a plurality of contacts;
 a rod disposed within the housing; and
 an encoded member configured:
  to be rotatably supported inside the housing;
  to engage with the rod and to be rotatable with respect to the rod; and
  to be axially constrained with respect to the housing such that axial advancement of the rod in a first direction relative to the housing causes rotation of the encoded member, wherein the outer surface of the encoded member is provided with a plurality of tracks together forming an encoder, each track comprising conductive segments and non-conductive segments and wherein the encoded member is supported in the housing such that each track is engaged by a respective one of the plurality of contacts.

The outer surface of the rod may be provided with a first thread having a first pitch and a second thread having a second pitch and wherein the first thread is configured to engage with a threaded aperture of the housing such that the rod rotates in a first rotational direction and advances in a first axial direction relative to the housing when an axial force is applied to the rod.

The first pitch and the second pitch may be different and the encoded member may be configured to engage with the second thread. Alternatively, the first pitch and the second pitch may be equal.

The first and second threads may be of opposite handedness and the encoded member may be configured to engage with the second thread of the rod such that rotation of the rod in a first rotational direction causes rotation of the encoded member in a second rotational direction.

The conductive and non-conductive segments of the plurality of tracks may be arranged as a Gray code. All of the conductive segments of the plurality of tracks may be electrically connected together.

The device may further comprise a user actuatable plunger configured, when depressed:
 to cause an axial force to be exerted on the rod in the first axial direction; and
 to cause expulsion of a drug from the drug delivery device.

The device may further comprise a processor configured to cause an electrical signal to be applied to a power contact located adjacent to a last one of the plurality of contacts and to monitor signals at the plurality of contacts. The power contact may be configured to engage with a power track located adjacent to a last one of the plurality of tracks. The power track may comprise only conductive segments.

The processor may be configured to monitor signals at a plurality of contacts.

The processor may be configured to monitor signals at the plurality of contacts only when the user actuatable plunger is depressed.

The processor may be configured to determine an amount of rotation of the encoded member from the signals.

The processor may be configured to determine a dispensed drug dose from the amount of rotation of the encoded member. The processor may be configured to cause the determination of the dispensed drug dose to be stored in a memory of the device. The processor may be configured to cause the determination of the dispensed drug dose to be displayed on a display of the device.

BRIEF DESCRIPTION OF THE DRAWINGS

Embodiments will now be described, by way of example only, with reference to the accompanying drawings, in which.

DETAILED DESCRIPTION

Figure 1:
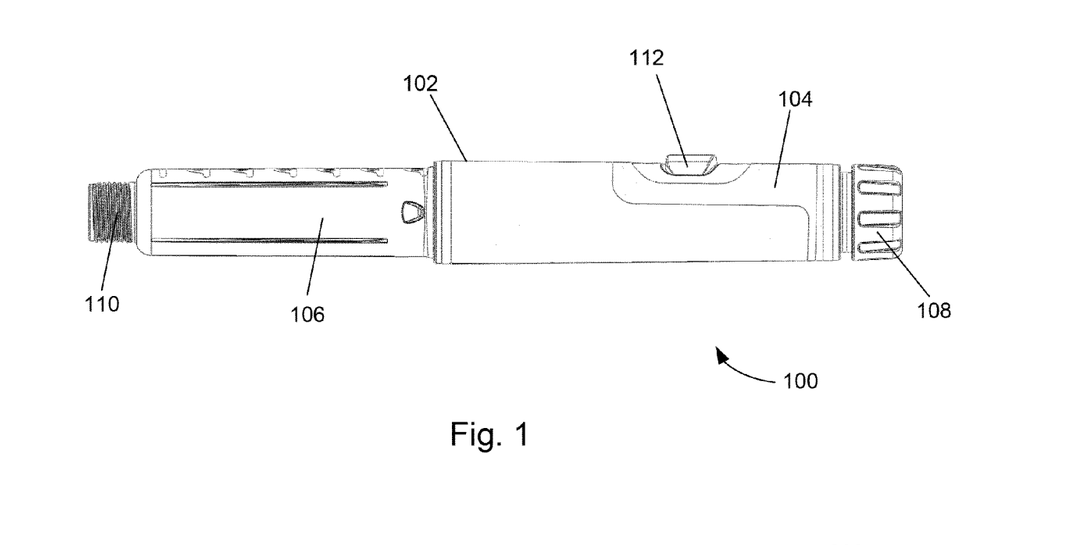
FIG. 1 shows an external view of a drug delivery device suitable for implementing the present invention.

Referring firstly to FIG. 1, an external view of a drug delivery device 100 according to embodiments of the invention is shown. The device 100 shown in FIG. 1 is a pen type injection device, having an elongate cylindrical shape, for setting and delivering a medicament, such as insulin. The device 100 comprises a housing 102 having a first housing part 104 and a second housing part 106. A rotatable dial 108 is located at a first (or proximal) end of the first housing part 104. The rotatable dial 108 has substantially the same outer diameter as the first housing part 104. The second housing part 106 may be detachably connected to the second end of the first housing part 104. The second housing part 106 is configured to have a needle (not shown) or similar drug delivery apparatus attached to it. To achieve this, the second (or distal) end of the second housing part 106 may have a threaded portion 110. The threaded portion 110 may have a smaller diameter than the remainder of the second housing part 106.

A display 112 may be located on the first housing part 104. The display 112 may be an LCD display, a segmented display or any other suitable type of display. The display 112 may cover a recess (not shown) in the first housing portion 104. A number of electronic components, described in greater detail with reference to FIG. 2, may be disposed in the first housing part 104, for example underneath the display 112.

The first housing part 104 contains a drug dose setting and delivery mechanism. The second housing part 106 contains a drug cartridge 114 (shown in FIG. 3). The drug contained in the drug cartridge 114 may be a medicament of any kind and may preferably be in a liquid form. The drug delivery mechanism of the first housing part 104 may be configured to engage with the drug cartridge 114 of the second housing part 106 to facilitate expulsion of the drug. The second housing part 106 may be detached from the first housing part 104 in order to insert a drug cartridge 114 or to remove a used cartridge. The first and second housing parts 104, 106 may be connected together in any suitable way, for example with a screw or bayonet type connection. The first and second housing parts 104, 106 may be non-reversibly connected together in such a way as the drug cartridge 114 is permanently contained with the drug delivery device 100. Further the first and second housing parts 104, 106 may form part of a single housing part.

The rotatable dial 108 is configured to be rotated by hand by a user of the drug delivery device 100 in order to set a drug dose to be delivered. The dial 108 may be connected to an internal threading system which causes the dial 108 to be displaced axially from the housing 102 as it is rotated in a first direction. The dial 108 may be rotatable in both directions or only in a first direction. The device 100 is configured, once a drug dose has been set by rotation of the rotatable dial 108, to deliver the set drug dose when a user exerts an axial force at the proximal end of the device. The rotatable dial 108 may support a button or plunger (not shown) which must be depressed in order to deliver the set drug dose. The display 112 may be configured to display information on the drug dose which has been set and/or delivered. The display 112 may further show additional information, such as the actual time, the time of the last usage/injection, a remaining battery capacity, one or more warning signs, and/or the like.

Figure 2:
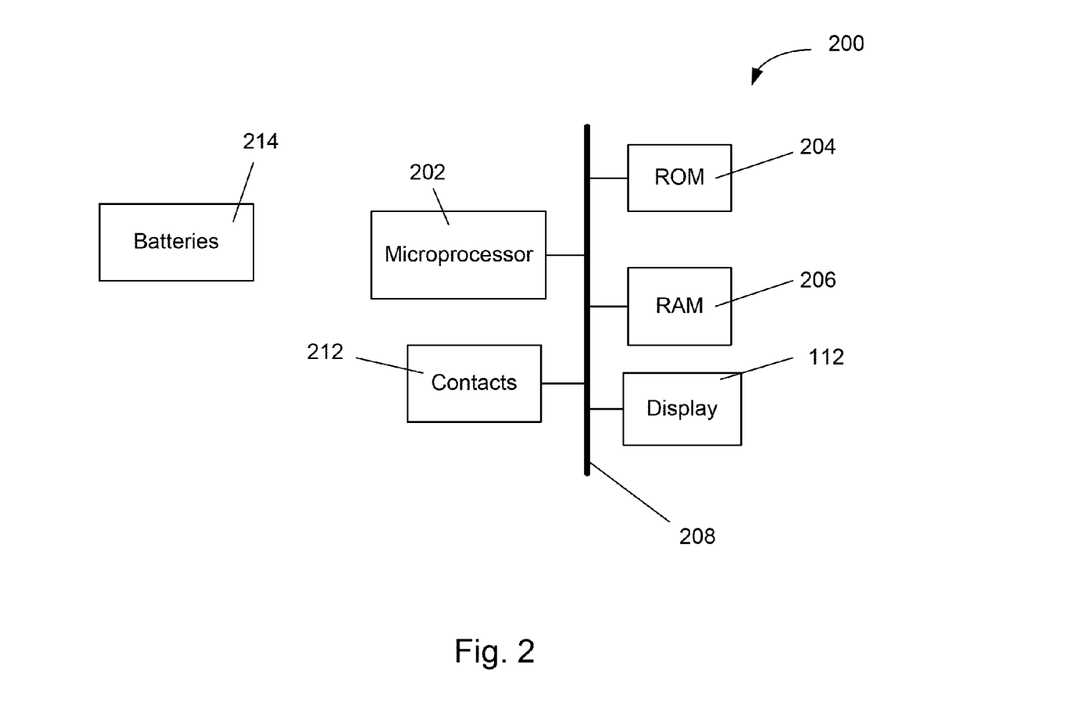
FIG. 2 shows a schematic diagram of some of the electronic components present in the drug delivery device of FIG. 1.

Referring now to FIG. 2, a schematic diagram of electrical circuitry 200 forming part of the drug delivery device 100 is shown. The circuitry 200 comprises a microprocessor 202, a non-volatile memory such as a ROM 204, a volatile memory such as a RAM 206, the display 112, contacts 212 and a bus 208 connecting each of these components. The circuitry 200 also comprises batteries 214 or some other suitable source of power for providing power to each of the components.

The circuitry 200 may be integral with the device 100. Alternatively, the circuitry 200 may be contained within an electronic module that can be attached to the device 100. In addition, the circuitry 200 may comprise additional sensors, such as optical or acoustical sensors.

The ROM 204 may be configured to store software and/or firmware. This software/firmware may control operations of the microprocessor 202. The microprocessor 202 utilises RAM 206 to execute the software/firmware stored in the ROM to control operation of the display 112. As such the microprocessor 202 may also comprise a display driver.

The batteries 214 may provide power for each of the components including the contacts 212. The supply of electricity to the contacts 212 may be controlled by the microprocessor 202. The microprocessor 202 may receive signals from the contacts 212 and thereby determine when the contacts are energised, and is configured to interpret these signals. Information may be provided on the display 112 at suitable times by operation of the software/firmware and the microprocessor 202. This information may include measurements determined from the signals received by the microprocessor 202 from the contacts 212.

A number of contacts 212 may be present in the device 100. In a preferred embodiment, six contacts 212 are present and may be addressed individually by the microprocessor 202. The contacts 212 may be mounted on an inner surface of the housing 102.

Figure 3:
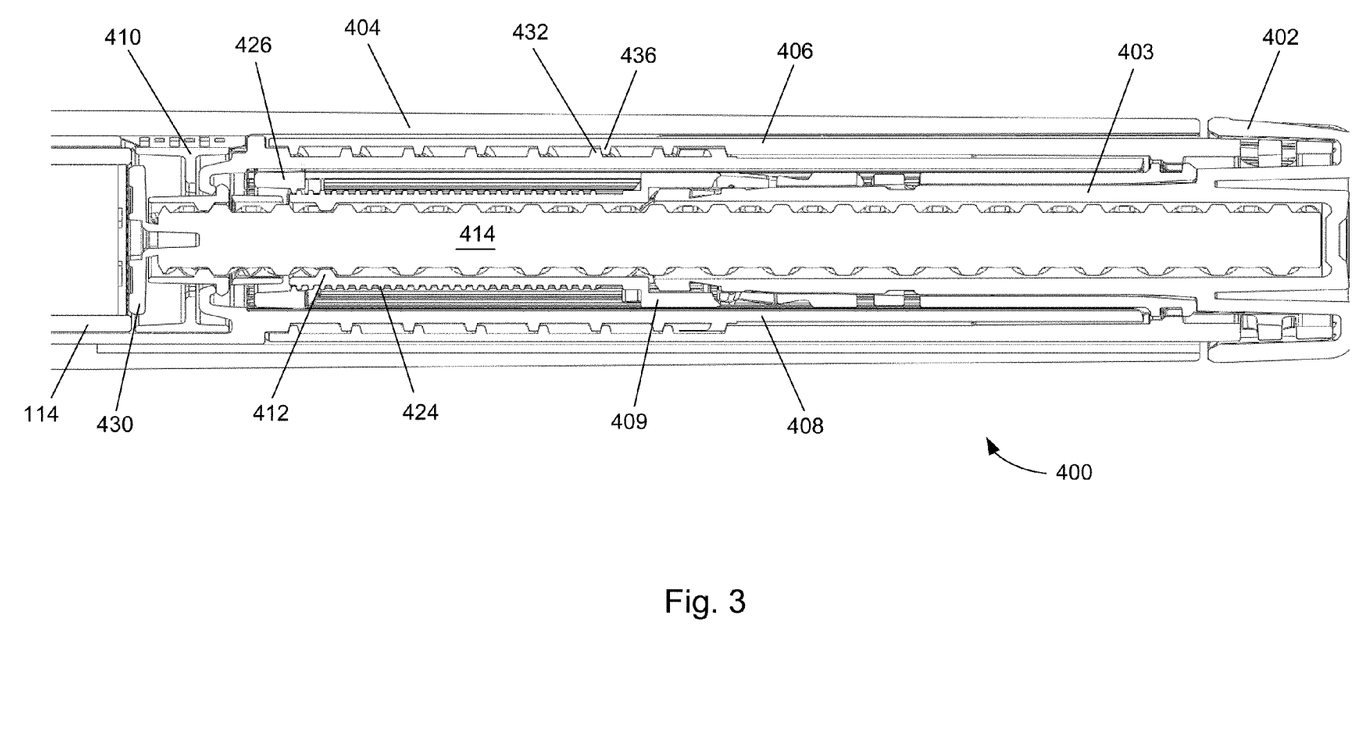
FIG. 3 is a schematic showing an overview of an internal mechanism of a drug delivery device suitable for use with the invention.
Figure 4:
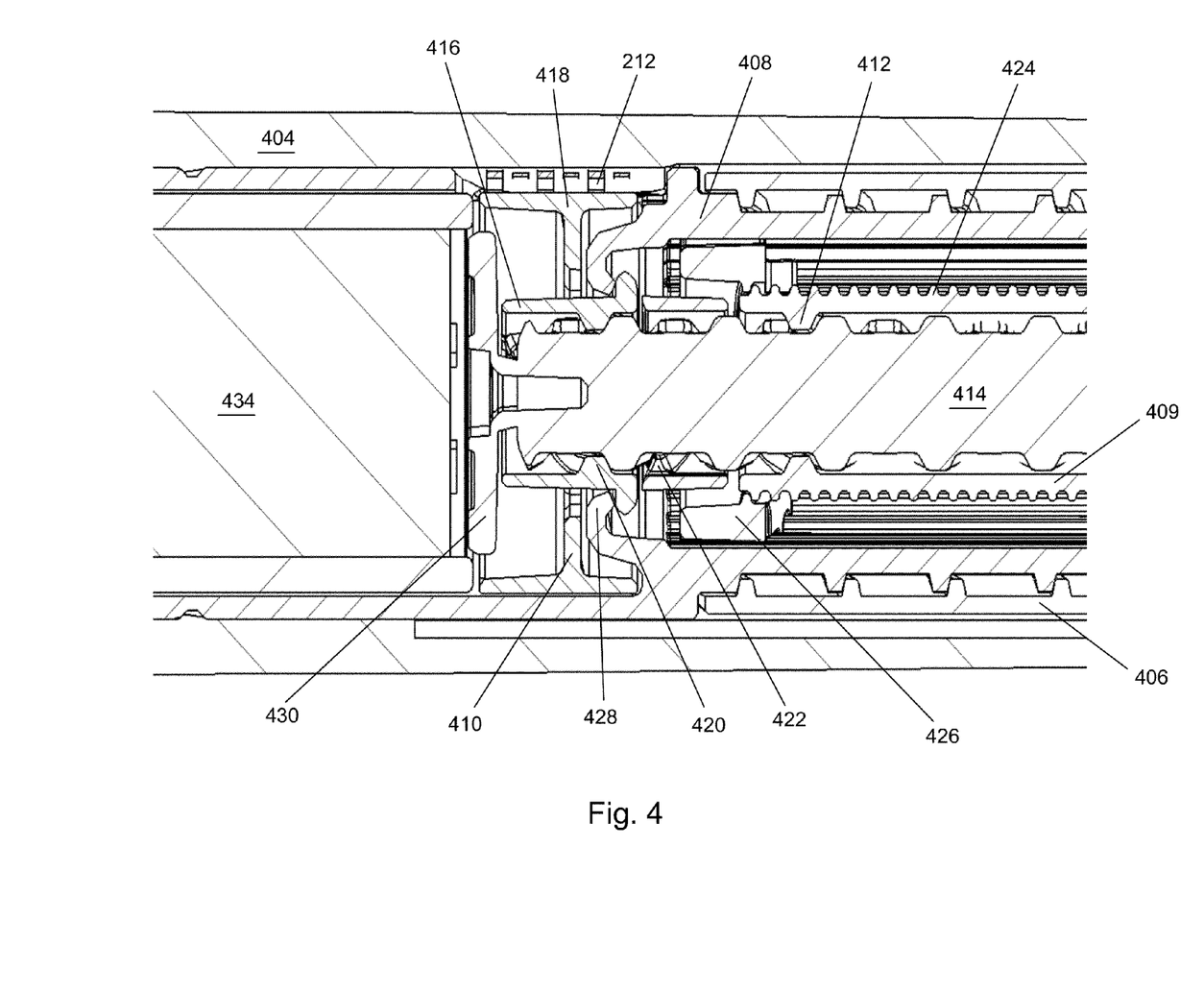
FIGS. 4 and 5 show detailed sectional and perspective views respectively of a part of the mechanism of FIG. 3.
Figure 5:
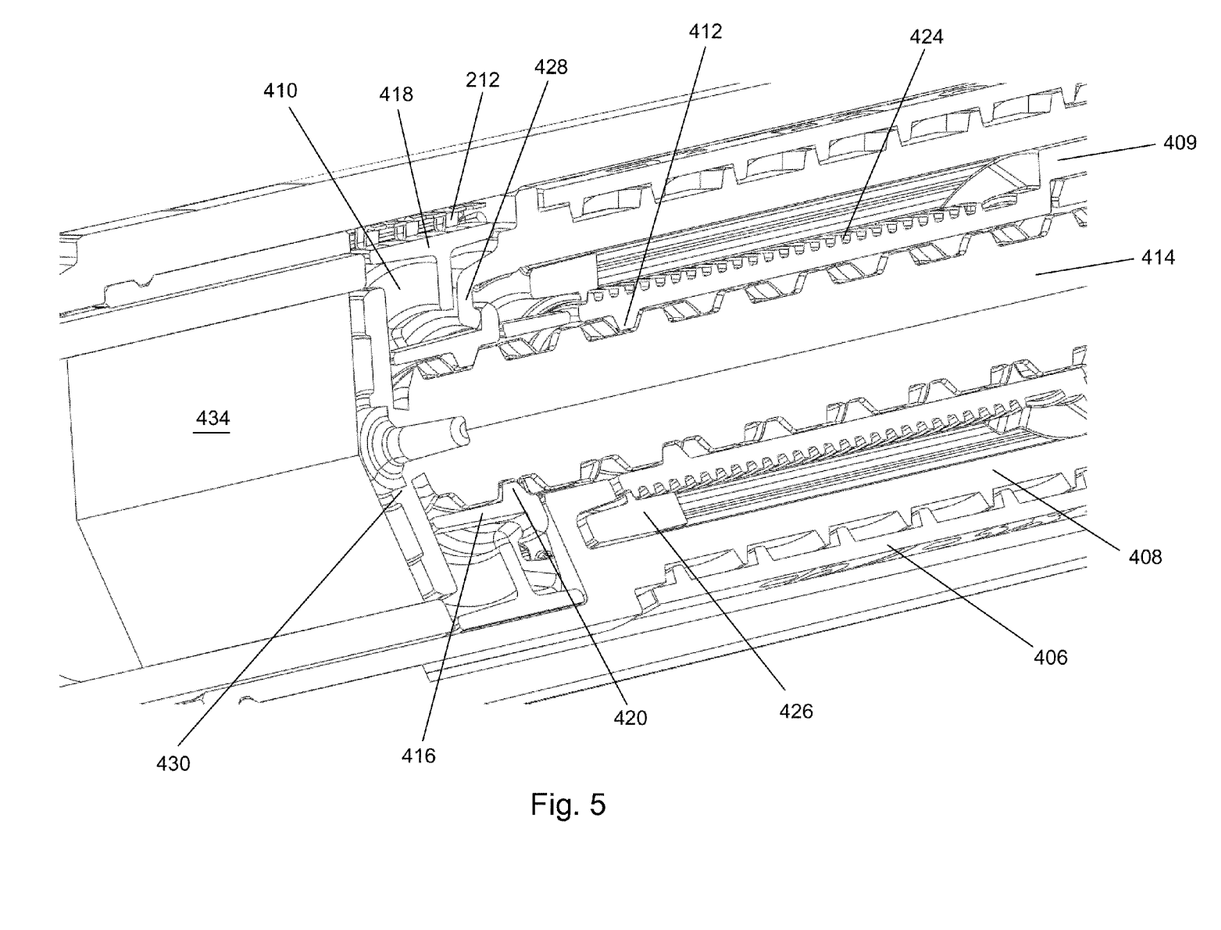

A fuller explanation of the operation of the dose setting and delivery mechanism supported within the second housing part 106 will now be given with reference to FIGS. 3 to 5. FIG. 3 is a cross-sectional view of a dose setting mechanism 400 of a drug delivery device. FIGS. 4 and 5 show detailed cross-sectional and perspective views respectively of a part of the mechanism including an encoded lead screw nut.

The dose setting mechanism 400 comprises an outer housing 404, an inner housing 408, a spindle 414 (also referred to as a lead screw or rod) and an encoded lead screw nut 410. The encoded lead screw nut 410 constitutes an encoded member and is referred to in this specification also as an encoded nut, a lead screw nut, or simply a nut. The outer and inner housings 404, 408 are preferably hollow cylindrically shaped members arranged concentrically. The spindle 414 is disposed centrally within the mechanism 400. The encoded nut 410 is located at a distal end of the mechanism 400. A number sleeve 406 is disposed between the outer and inner housings 404, 408. The number sleeve 406 is also preferably a hollow cylindrically shaped member. The inner housing 408 comprises a groove or thread 432 provided along an external surface of the inner housing 408. A helical protrusion or thread 436 provided on an inner surface of the number sleeve 406 is rotatably engaged with this thread 432. The number sleeve 406 preferably has numerals printed on its outer surface. The number sleeve 406 may have numbers representing a number of units of a dialled dose.

A dose dial grip 402 is located at a proximal end of the outer housing 404. The dose dial grip 402 is disposed about an outer surface of a proximal end of the number sleeve 406. An outer diameter of the dose dial grip 402 preferably corresponds to the outer diameter of the outer housing 404. The dose dial grip 402 is coupled to the number sleeve 406 in such a way as to prevent relative longitudinal movement between these two components and to allow the number sleeve 406 to rotate relative to the dose dial grip 402 in only one direction. The dose dial grip 402 is represented in the external view of FIG. 1 by the rotatable dial 108. As can be seen in FIG. 3, the dose dial grip 402 is integral with a dose dial sleeve 403 which extends for some distance within the mechanism 400 and is immediately adjacent to the spindle 414. In some embodiments the dose dial grip 402 may support a dose button (not shown) which has a sprung bias in a proximal direction and is configured to be depressed into the dose dial grip 402 by a user of the device 100.

The dose setting mechanism 400 also comprises a driver 409 which extends about the spindle 414. The proximal end of the driver 409 abuts the distal end of the dose dial sleeve 403 such that relative longitudinal movement between the dose dial sleeve and grip 403, 402 and the driver 409 is prevented. The driver 409 may also be coupled to the sleeve 403 in such a way as to prevent relative rotational movement between these components in at least one rotational direction. The driver 409, dose dial sleeve 403 and dose dial grip 402 may together be termed "a plunger". Alternatively, only the dose dial grip 402 and/or a button (not shown) supported by the dose dial grip 402 may be referred to as the plunger.

The outer surface of the spindle 414 has at least two helical grooves or threads. In the embodiment depicted, the spindle 414 has two opposite handed overlapping threads that preferably extend over at least a majority of a length of the spindle 414. Each thread is effectively continuous over a number of turns. In the depicted embodiment both of these threads are double start threads. In one preferred arrangement, a first thread of the spindle 414 engages with the inner housing 408 and a second thread of the spindle 414 engages with the driver 409.

The driver 409 has a first groove form 412 at its distal end and on the inner surface of the driver 409. Preferably, the first groove form 412 comprises a partial male groove form that engages the second thread of the spindle 414. Preferably, this first groove form 412 comprises a groove form of less than one turn. A portion of the outer surface of the driver 409 at the distal end comprises a thread 424. The mechanism also has a dose limiter 426 which comprises a nut. The dose limiter 426 has an internal helical protrusion matching the thread 424 on the outer surface of the driver 409. In one preferred arrangement, the outer surface of the dose limiter 426 and an internal surface of the inner housing 408 are keyed together by way of splines. This prevents relative rotation between the dose limiter 426 and the inner housing 408 while allowing relative longitudinal movement between these two components.

The first thread of the spindle 414 is engaged by the inner housing 408. At a distal end of the mechanism 400 the inner housing 408 comprises a ring of material of reduced diameter relative to the main body of the inner housing 408. The spindle 414 passes through the aperture formed by this ring. The inner surface of this ring has a helical protrusion 422 which engages with the first thread of the spindle 414. Therefore, the spindle 414 is constrained to rotate in a first rotational direction when it advances axially in a distal direction. The inner housing 408 also has one or more extensions 428 having a hook shaped cross-section. In some embodiments, the extension 428 is a single, ring shaped protrusion. In some other embodiments, a number of partial ring shaped extensions 428 are present. The extensions 428 act to retain the encoded lead screw nut 410 in order to prevent any longitudinal movement of the nut 410 relative to the inner housing.

The dose setting mechanism 400 described above is merely one example of a mechanism suitable for supporting the encoded lead screw nut 410 and for implementing the present invention. It will be apparent to the skilled person that other mechanisms may also be suitable. For example, a mechanism which does not include an inner housing 408, but in which the encoded lead screw nut 410 is retained by the outer housing 404 or by another component would be equally suitable.

A user of the device 100 sets or "dials" a dose by gripping and rotating, in a first rotational direction, the dose dial grip 402. The dose dial sleeve 403 rotates with the dose dial grip 402 and is coupled to the driver 409 such that the driver 409 also rotates. As the driver 409 is threaded to the second thread of the spindle 414 via the groove form 412, rotation of the driver 409 causes both the driver 409 and dial 402 to move axially in a proximal direction. The spindle 414 remains stationary during dialling of the device 100. The number sleeve 406 is coupled to the dose dial grip 402 such that when a user rotates the dose dial grip 402, the number sleeve 406 also rotates. As the number sleeve 406 is rotated in a first rotational direction, it also moves axially in a proximal direction due to its threaded connection to the inner housing 408. The lead of the second thread of the spindle 414 and of the inner housing thread 432 are the same such that the number sleeve 406, dose dial sleeve 403 and driver 409 all move axially at the same rate during dialling.

During dialling the dose limiter nut 426 moves longitudinally in a proximal direction relative to the inner housing 408 due to its threaded connection to the driver thread 424 and splined connection to the inner housing 408. The body of the driver 409 has a larger diameter beyond the driver thread 424 portion. The dose limiter 426 is configured to prevent a user of the device 100 from dialling a greater dose than remains in the drug cartridge. When a user dials the maximum drug dose (or the maximum remaining drug dose), the dose limiter 426 abuts the heel in the driver body where the diameter increases, thus preventing any further dialling out.

When the drug delivery device is being dispensed, the user applies an axial load to the dose dial grip 402 (or dose button if present). The driver 409 is prevented from rotating in a second rotational direction (opposite to the direction of the dialling) relative to the inner housing 408. However the driver is able to rotate in both rotational directions relative to the spindle 414. Therefore, when an axial load is applied to the dose dial grip 402, the spindle 414 is forced to advance axially in a distal direction by the driver 409. The number sleeve 406 is free to rotate in a second rotational direction relative to the dose dial grip 402. Therefore, as the dose dial grip 402 is advanced axially during dispensing, the number sleeve 406 rotates in a second direction, back to its starting (zero dose) position. As the spindle 414 advances, it rotates in a first rotational direction due to the threaded connection between the helical protrusion 422 of the inner housing and the first thread of the spindle 414. At the distal end of the spindle 414 is a bearing 430 which is secured to, but free to rotate relative to, the spindle 414. This bearing 430 abuts a bung 434 of the drug cartridge 114. Medicament is caused to be expelled from the cartridge 114 when this bung 434 is advanced.

In some embodiments, the pitches of the first and second threads of the spindle 414 are certain discrete proportions of each other such as the same pitch 1:1 or ratios such as 2:1, 1.66:1. It is advantageous that the ratio of the pitches of the first and second threads of the spindle 414 be a discreet multiple. One reason for this is that it can ensure that the threads of the spindle 414 cross over one another at regular angular positions. In the case of the spindle 414 illustrated in FIGS. 3 to 5, the pitch of the first thread is equal to that of the second thread. One advantage of this configuration is that it ensures that with two equally spaced starts for each thread, the threads cross over one another every 90 degrees. With the typical thread pitches used, this enables the spindle 414 to be moulded with a two slide open and shut tool construction. Of course other ratios may also be used. However, as one of skill in the art will recognise, there are a certain limited number of range of ratios that will enable the spindle 414 to be moulded easily with injection mould tooling. Alternatively if the ratio is 2:1, the threads cross over every 60 degrees and with carefully designed thread forms this ratio can still be moulded with an open and shut mould tool construction.

The advance of the spindle 414 in the distal direction when the driver 409 is advanced during dose administration is dependent on the magnitude of the pitch of the first and the second threads of the spindle 414. Therefore, the dose dispensed is linked only to the dimensions of the spindle 414 and no other component. The spindle 414 could therefore be made from a material that has a very low or consistent shrinkage to improve dose accuracy.

Furthermore, if the driver 409 engages the second thread of the spindle 414 only at the distal end of the driver 409 (in contrast to designs where the driver engages a spindle helix over a larger portion of the spindle), the spindle 414 can extend in a proximal direction beyond the end of the driver 409. One benefit of such a driver and spindle arrangement is that it enables the overall length of the drug delivery device to be reduced.

The inner housing 408 may be made from an engineering plastic that minimizes friction between the number sleeve thread 436 and the inner housing thread 432. Friction between the inner housing extensions 428 and the encoded lead screw nut 410 may also be reduced. For example, one such an engineering plastic could comprise Acetal. However, those skilled in the art will recognise that other comparable engineering plastics having a low coefficient of friction could also be used. Using such an engineering plastic enables the material for the outer housing 404 to be chosen for aesthetic or tactile reasons with no friction related requirements since the outer housing 404 does not engage any moving components during normal operation.

An advantage of a dose setting mechanism 400 comprising an inner housing 408 is that the illustrated dose setting mechanism 400 can be modified easily from a non-resettable device into a re-settable device. International patent application number WO 2010/139640 A1, which is incorporated herein by reference, describes a re-settable dose setting mechanism which could be modified to incorporate the present invention.

Figure 6:
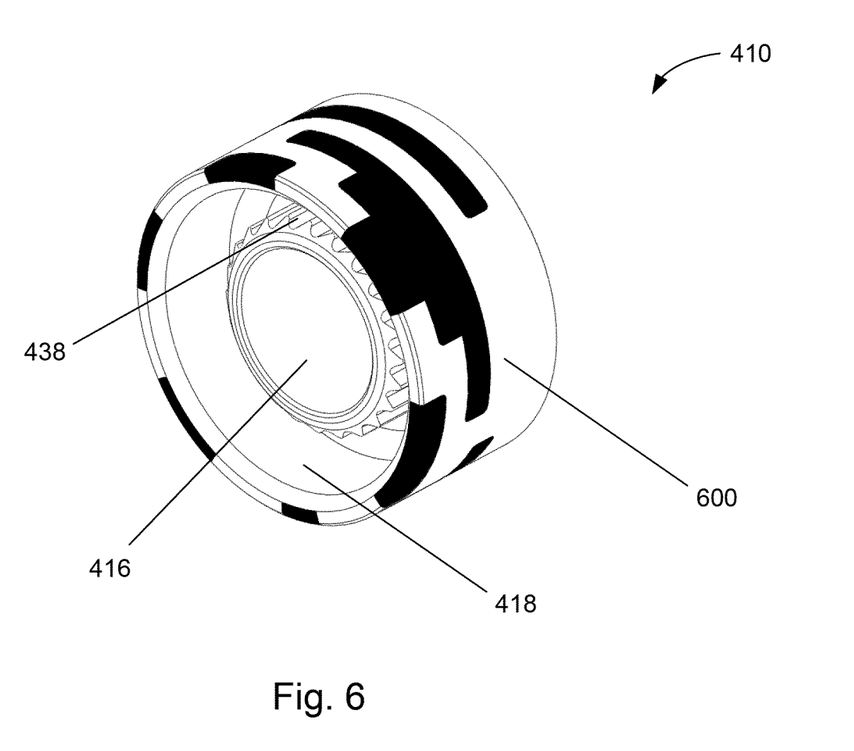
FIG. 6 shows an encoded nut with encoded tracks on an outer surface according to an embodiment of the invention.

Referring also to FIG. 6, the mechanism 400 comprises an encoded lead screw nut 410. The lead screw nut 410 is formed of two concentric cylinders, hereafter referred to as the inner section 416 and the outer section 418, joined by a ring of material. The ring of material joining the inner and outer sections 416, 418 may be continuous or alternatively may comprise several partial rings. An inner surface of the inner section 416 of the nut 410 has a groove form 420 (not visible in FIG. 6). The groove form 420 engages with the second thread of the spindle 414.

An outer surface of the inner section 416 of the nut 410 may comprise a number of biasing teeth 438 (as shown in FIG. 6). These teeth may be engaged by one or more biasing elements (not shown) which ensure that there is no rotational float of the nut 410 by constraining it to discreet rotational positions. Alternatively, the biasing feature may be omitted and the outer surface of the inner section 416 of the nut 410 may be smooth, as shown in FIGS. 3-5.

As the encoded nut 410 is constrained axially within the housing, but threaded to the second thread of the spindle 414, it rotates when the spindle 414 is advanced during dispensing of the drug delivery device 100. However, as described above, the first thread of the spindle 414 is threaded to a helical protrusion 422 on the inner housing, causing the spindle 414 to rotate in a first rotational direction as it advances axially in a distal direction. Because the first and second threads of the spindle 414 are of opposite handedness (i.e. opposite directions), the encoded nut 410 rotates in a second rotational direction and at double the angular velocity of the spindle 414 during dispensing.

This operation may be better understood by considering separately the results of rotation and axial advancement of the spindle 414. If the spindle 414 were to advance axially within the housing without rotating, then the encoded nut 410 (which is still constrained axially within the housing) would rotate in a second rotational direction due to its threaded connection with the second thread of the spindle 414. The speed of this rotation is determined by the pitch, or more precisely the lead of this threaded connection. If the spindle 414 were to rotate, without advancing axially within the housing, in a first rotational direction, the encoded nut 410 would also be caused to rotate in a second rotational direction due to the opposite handedness of the second thread of the spindle from the first. Therefore, when the spindle 414 both advances and rotates in a first rotational direction, the encoded nut 410 is caused to rotate at twice the speed of the spindle 414 in a second rotational direction.

The double rotational speed of the encoded nut 410 relative to the spindle 414 is due to the equal and opposite pitches of the first and second threads of the spindle 414. However the pitches of the first and second threads do not have to be equal. While certain ratios of the first and second thread pitches may be advantageous in terms of manufacturing ease, the skilled person will appreciate that any ratio may be used. For example, if the ratio were 2:1 such that the pitch of the second thread were half that of the first thread then the encoded nut 410 would rotate at four times the angular velocity of the spindle 414.

The outer surface of the outer section 418 of the nut 410 is provided with a number of tracks 600 arranged adjacent to one another. Each track 600 comprises conductive and non-conductive segments. In FIG. 6, the conductive segments are shown as white areas and the non-conductive segments are shown as black areas. The lead screw nut 410 may be made of a metal material such as brass. The nut 410 may be machined such that the outer surface has channels and ridges which, when the channels are filled with a non-conductive material, form the tracks 600. In some embodiments, the nut 410 has six tracks 600.

Referring again to FIGS. 4 and 5, the contacts 212 are supported on an inner surface of the outer housing 404, beyond a distal end of the inner housing 408. Each of the contacts 212 is configured to engage a respective one of the tracks 600 on the encoded nut 410. The contacts 212 may be sprung such that when the device 100 is fully assembled, the contacts 212 are biased against the outer surface of the encoded lead screw nut 410. This ensures that a stable connection between the contacts 212 and the conductive regions of the tracks 600 is maintained.

The outer housing 404 may be provided with a recess (not shown), either in the inner or outer surface, at the location of the contacts 212. This recess may provide a space in which the microprocessor 202, ROM 204, RAM 206, display electronics and batteries 214 may be contained. Conductive tracks or wires may join the contacts 212 to the microprocessor 202. In one exemplary embodiment, a recess may be provided in the outer surface of the outer housing 404 and may be configured to receive an electronic module containing the components listed above. Contacts on the underside of this module may engage with the contacts 212, or with conductive regions in communication with the contacts 212, in order to facilitate the connection to the microprocessor 202.

The microprocessor 202 is configured to address each of the contacts 212 individually. The microprocessor 202 may also be configured to control the flow of electricity from the batteries 214 to each contact. In a preferred embodiment, there are six contacts 212 which engage six tracks 600. The sixth track may be a power or ground track comprising only conductive segments. Power may be supplied to the sixth track via the sixth contact. In preferred embodiments, all of the conductive segments are electrically connected together. Therefore, when power is supplied to the power track (or any other conductive segment), all of the conductive segments are energized. The microprocessor 202 may therefore cause a power signal to be applied to the sixth contact and detect signals from each of the other contacts 212 in order to determine the pattern of conductive and non-conductive segments underneath the contacts 212 at any time.

During dispensing of the device 100, the encoded lead screw nut 410 rotates as described above. During this process a voltage may be applied to the power track and signals monitored at the other contacts 212. In this manner, an amount of medicament which is dispensed may be determined and recorded. It is often necessary for a user of such a drug delivery device 100 to adjust the medicament dose based at least in part on their previous doses. It is therefore advantageous to accurately and automatically record all dispensed doses. Having the encoded nut 410 rotate at twice the angular velocity of the spindle 414 during drug dispensing means that each of the segments comprising the tracks 600 can be twice as large relative to an equivalent encoded nut which rotates at the same speed as the spindle 414. An advantage of this feature is that the reliability of the dose position determination is increased. Some construction cost savings may also be made as the tracks 600 may not need to be manufactured as precisely is order to obtain a desired level of dose determination accuracy. Alternatively, the segments comprising the tracks 600 can be of the same size as of a nut which rotates at the same speed as the spindle 414. This embodiment results in an increased resolution of the detection of the rotation of the spindle and therefore of the dispensed doses.

Having determined the drug dose which has been dispensed, the microprocessor 202 may store the result in the ROM 204. The display 112, if present, may be controlled to display the result of the dispensed dose determination. The display 112 may display the result of the dispensed dose determination for a predetermined time, for example 60 seconds. Alternatively or in addition, the dispensed dose history may be retrieved electronically from the ROM 204 by a user of the device 100 or by a health care professional.

Although the lead screw nut 410 allows a dose history to be easily and accurately recorded, the user may still need to be able to see an indication of the dialled dose. The display 112 may display an indication of the current dialled dose. Alternatively or in addition, a window (not shown) may be provided in the outer housing 404 of the drug delivery device 100. This window may allow numbers printed on the number sleeve 406 to be seen by a user of the device 100 while dialling a dose. These numbers may be arranged on the surface of the number sleeve 406 in a helix such that as the number sleeve rotates and moves axially in a proximal direction, a number is located directly underneath the window.

Figure 7:
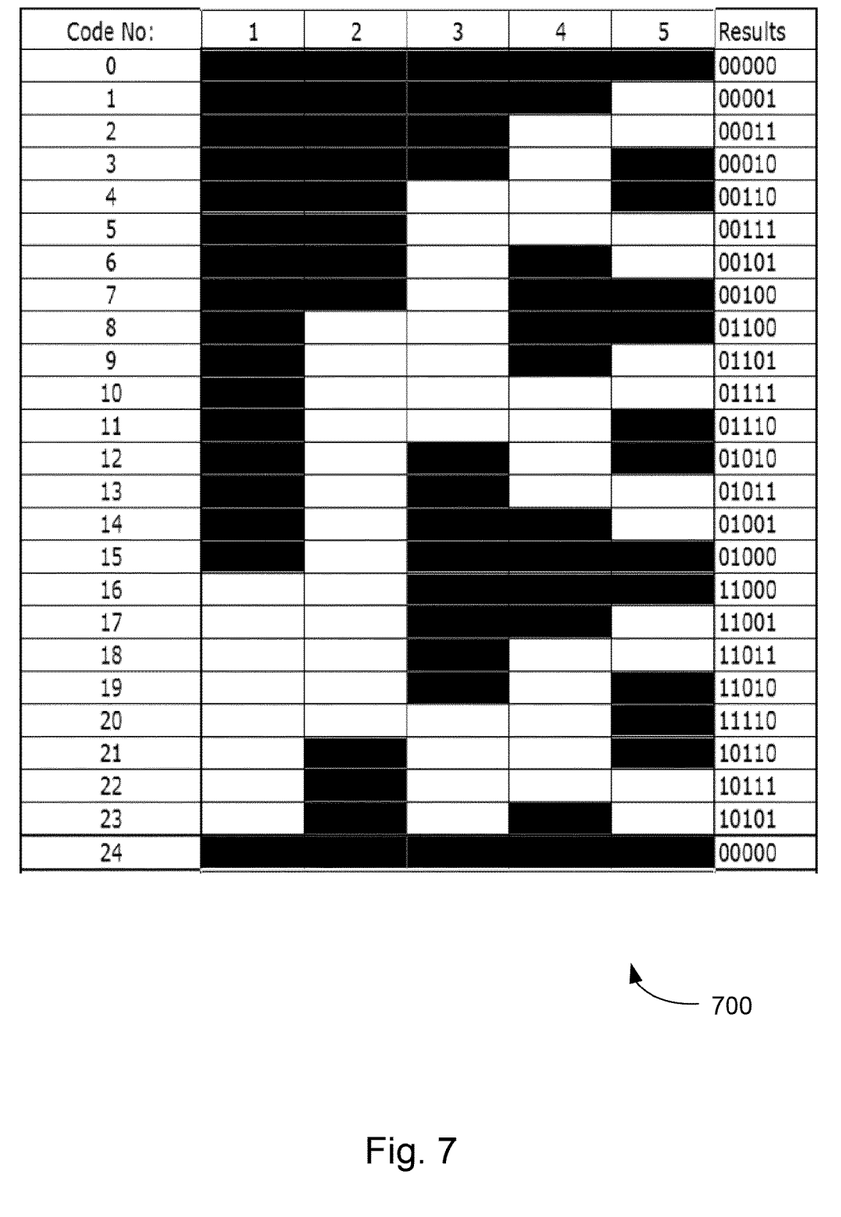
FIG. 7 is a table illustrating an exemplary layout of conductive and non-conductive segments forming the encoded tracks on the surface of the encoded nut.

FIG. 7 shows a table 700 illustrating an exemplary layout of conductive and non-conductive segments forming the tracks 600 on the encoded nut 410. The conductive and non-conductive segments of the tracks 600 may be arranged to form a type of Gray code, or reflected binary code. A Gray code is a binary coding system in which only one binary bit changes value between each successive encoded value.

The columns labelled 1 to 5 represent the first five tracks 600 of the encoded nut 410. A code digit with a value of "1" is represented by a conductive (white) segment and a value of "0" is represented by a non-conductive (black) segment. The last column shows the result obtained at the first five contacts 212 in each case and the first column shows the dose position that this result encodes. The sixth track is not shown as it acts only as a power supply track. Having five tracks 600 results in a five bit encoding system which allows up to 25=32 unique values to be encoded. Where the drug delivery device 100 shown in FIG. 1 is an insulin pen type injection device, users may need to set an insulin dose of between 1 and 80 International Units. However, the invention is equally valid for any number of tracks. For example a seven bit encoding system would allow for the full 0-80 unit dial-able dose for an insulin pen type injection device to be absolutely encoded.

Not all of the available encoding combinations may be used. The table 700 shows that the tracks 600 of the encoded nut 410 may each have 24 segments such that 24 dose units equates to one complete turn of the nut 410. Using fewer segments means that each segment occupies a larger area on the surface of the nut 410. However the microprocessor 202 may still determine that a dose of greater than 23 units has been delivered by detecting a number of complete revolutions of the encoded nut 410. A dose value of "24" is encoded by "00000", as is a dose value of "0". During dispensing of the device 100, when the dose remaining decreases from "24" to "23", the microprocessor 202 sees a change in three of the five contacts. Thus it is easy for the microprocessor 202 to determine that a full revolution of the encoded nut 410 has occurred. In this manner, the microprocessor 202 may determine any delivered dose value by counting full rotations of the nut and/or decoding partial rotations.

Arrangements of the encoded lead screw nut 410 which do not have a dedicated power track are also possible. It can be seen from the table 700 that if any one of the conductive segments has a signal applied to it, then all of the other conductive segments will also be energized. Therefore, a voltage may be provided to one of the contacts 212, and the output of the other contacts 212 detected. A cyclic check on several of the contacts 212 may need to be performed if one or more of the contacts 212 is located over a non-conductive segment when a voltage is applied to it.

Figure 8:
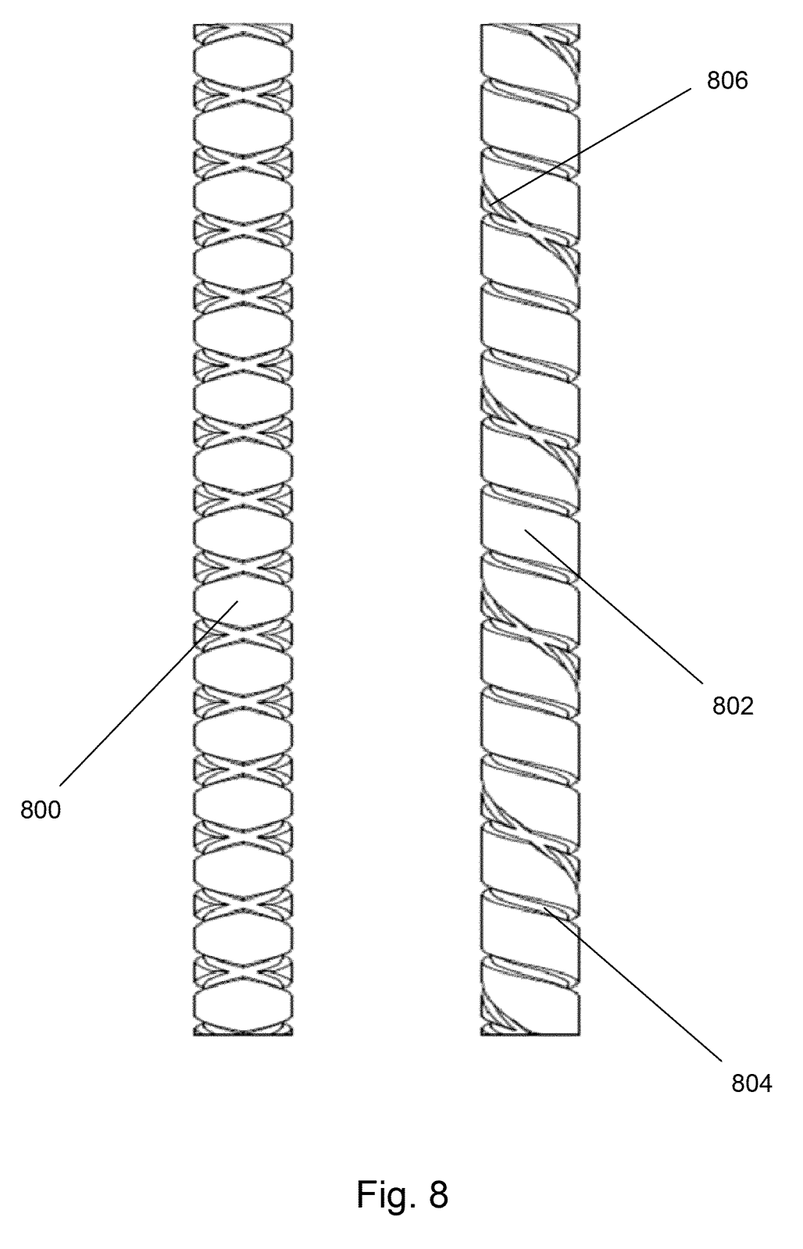
FIG. 8 shows two examples of spindles suitable for use in the invention.

FIG. 8 illustrates two different spindles. The first spindle 800 is the same as the spindle 414 shown in FIGS. 3 to 5. This spindle 800 has two overlapping threads of equal and opposite pitch, although other pitch ratios may be used. As described above with respect to FIGS. 3 to 5, in some embodiments a first thread of the spindle 800 may be engaged with the inner housing 408 and a second thread of the spindle 800 may be engaged with the driver 409 and encoded leadscrew nut 410. In some other embodiments, the driver 409 may be engaged with the first thread of the spindle 800 and only the encoded nut 410 may be engaged with the second thread.

The second spindle 802 shown in FIG. 8 has an alternative arrangement of threads. The spindle 802 has two threads with the same handedness, but different pitches. In the spindle 802 shown, the second thread 806 has a pitch three times that of the first thread 804. In some embodiments, the first thread 804 may be engaged by the inner housing 408 and the second thread 806 may be engaged by the driver 409 and the encoded nut 410. It will be appreciated that in embodiments in which the driver 409 engages the second thread 806, the pitch of the second thread 806 relative to the first thread 804 affects the sensitivity of the dose dialling mechanism. Therefore, the greater the pitch ratio, the less rotation of the dose dial is required to set a given dose.

In some other embodiments, the first thread 804 of the spindle 802 may be engaged by the driver 409 and the encoded nut 410 and the second thread 806 may be engaged by the inner housing 408. In these embodiments, the sensitivity of the dose dialling mechanism is increased and more rotation of the dose dial is required to set a given dose. An advantage of these embodiments is that the frictional force which must be overcome when a dose is being dispensed may be lessened due to the greater pitch of the second thread 806, with which the inner housing 408 is engaged.

Although the second spindle 802 is shown with two threads having a pitch ratio of 3:1, the skilled person will appreciate that any ratio of thread pitches may be used. Commonly used pitch ratios may include 4:1, 3:1, 2:1, 1.66:1 and 1.5:1.

It will be appreciated that the above described embodiments are purely illustrative and are not limiting on the scope of the invention. Other variations and modifications will be apparent to persons skilled in the art upon reading the present application. Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:
1. A drug delivery device comprising:
a housing;
a plurality of contacts;
a rod disposed within the housing; and
an encoded member configured:
  to be rotatably supported inside the housing;
  to engage with the rod and to be rotatable with respect to the rod; and
  to be axially constrained with respect to the housing such that axial advancement of the rod in a first direction relative to the housing causes rotation of the encoded member, wherein the outer surface of the encoded member is provided with a plurality of tracks together forming an encoder, each track comprising conductive segments and non-conductive segments and wherein the encoded member is supported in the housing such that each track is engaged by a respective one of the plurality of contacts.

2. A drug delivery device as claimed in claim 1, wherein the outer surface of the rod is provided with a first thread having a first pitch and a second thread having a second pitch and wherein the first thread is configured to engage with a threaded aperture of the housing such that the rod rotates in a first rotational direction and advances in a first axial direction relative to the housing when an axial force is applied to the rod.

3. A drug delivery device as claimed in claim 2, wherein the first pitch and the second pitch are different and wherein the encoded member is configured to engage with the second thread.

4. A drug delivery device as claimed in claim 2, wherein the first pitch and the second pitch are equal and wherein the encoded member is configured to engage with the second thread.

5. A drug delivery device as claimed in claim 2, wherein the first and second threads are of opposite handedness and the encoded member is configured to engage with the second thread of the rod such that rotation of the rod in a first rotational direction causes rotation of the encoded member in a second rotational direction.

6. A drug delivery device as claimed in claim 1, wherein the conductive and non-conductive segments of the plurality of tracks are arranged as a Gray code.

7. A drug delivery device as claimed in claim 1, wherein all of the conductive segments of the plurality of tracks are electrically connected together.

8. A drug delivery device as claimed in claim 1, the device further comprising a user actuatable plunger configured, when depressed:
to cause an axial force to be exerted on the rod in the first axial direction; and
to cause expulsion of a drug from the drug delivery device.

9. A drug delivery device as claimed in claim 1, wherein the device further comprises a processor configured to cause an electrical signal to be applied to a power contact located adjacent to a last one of the plurality of contacts and to monitor signals at the plurality of contacts.

10. A drug delivery device as claimed in claim 9, wherein the power contact is configured to engage with a power track located adjacent to a last one of the plurality of tracks and wherein the power track comprises only conductive segments.

11. A drug delivery device as claimed in claim 9, the device further comprising a user actuatable plunger configured, when depressed:
to cause an axial force to be exerted on the rod in the first axial direction; and
to cause expulsion of a drug from the drug delivery device, wherein the processor is configured to monitor signals at the plurality of contacts only when the user actuatable plunger is depressed.

12. A drug delivery device as claimed in claim 9, wherein the processor is configured to determine an amount of rotation of the encoded member from the signals.

13. A drug delivery device as claimed in claim 12, wherein the processor is configured to determine a dispensed drug dose from the amount of rotation of the encoded member.

14. A drug delivery device as claimed in claim 13, wherein the processor is configured to cause the determination of the dispensed drug dose to be stored in a memory of the device.

15. A drug delivery device as claimed in claim 13, wherein the processor is configured to cause the determination of the dispensed drug dose to be displayed on a display of the device.

* * * * *